United States Patent
Bouton

(10) Patent No.: US 11,234,608 B2
(45) Date of Patent: *Feb. 1, 2022

(54) EXTRAVASATION AND INFILTRATION DETECTION DEVICE WITH FLUID GUIDE PROVIDED ON A SUBSTRATE OF THE DETECTION DEVICE TO ADJUST FLUID RATE BASED ON DETECTION SIGNAL

(75) Inventor: Chad E. Bouton, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/241,203

(22) PCT Filed: Aug. 29, 2012

(86) PCT No.: PCT/US2012/052813
§ 371 (c)(1),
(2), (4) Date: Mar. 11, 2014

(87) PCT Pub. No.: WO2013/033174
PCT Pub. Date: Mar. 7, 2013

(65) Prior Publication Data
US 2014/0228686 A1 Aug. 14, 2014

Related U.S. Application Data

(60) Provisional application No. 61/530,436, filed on Sep. 2, 2011, provisional application No. 61/530,454, filed (Continued)

(51) Int. Cl.
*A61B 5/05* (2006.01)
*A61M 5/168* (2006.01)
(Continued)

(52) U.S. Cl.
CPC .......... *A61B 5/0507* (2013.01); *A61B 5/0022* (2013.01); *A61B 5/0537* (2013.01);
(Continued)

(58) Field of Classification Search
CPC ........... A61B 5/00; A61B 8/08; A61B 5/0022; A61B 5/0507; A61B 5/4875;
(Continued)

(56) References Cited

U.S. PATENT DOCUMENTS 3,657,656 A 4/1972 Cooper
3,779,079 A 12/1973 Snook
(Continued)

FOREIGN PATENT DOCUMENTS

CA 2470801 2/2003
CN 10048215 4/2009
(Continued)

OTHER PUBLICATIONS

Gupta, Vani; Office Action; U.S. Appl. No. 14/241,171; dated Mar. 2, 2016; United States Patent and Trademark Office, Alexandria, VA.
(Continued)

*Primary Examiner* — Serkan Akar
(74) *Attorney, Agent, or Firm* — Kevin J. Carroll; Grossman, Tucker, Perreault & Pfleger PLLC

(57) ABSTRACT

An integrated device of a patch and sensor assembly detects extravasation or infiltration. A transmitter is positioned to direct power into a body portion. A sensor is positioned to receive the power transmitted through the body portion. A substrate is attachable to an outer surface of the body portion and supports the transmitter and the sensor. A signal processor is coupled to the transmitter and the sensor for detecting a change in a fluid level in the body portion from extravasation or infiltration based on the power received by
(Continued)

the sensor. A power supply is coupled to the transmitter and the sensor. An indicator is responsive to the signal processor to indicate a detected change in a fluid level in the body portion from extravasation or infiltration.

17 Claims, 6 Drawing Sheets

Related U.S. Application Data on Sep. 2, 2011, provisional application No. 61/530,441, filed on Sep. 2, 2011.

(51) Int. Cl.
| | | |
|---|---|---|
| *A61B 5/053* | (2006.01) | |
| *A61B 8/08* | (2006.01) | |
| *A61B 5/00* | (2006.01) | |
| *A61B 5/0507* | (2021.01) | |
| *A61B 5/0537* | (2021.01) | |

(52) U.S. Cl.
CPC .......... *A61B 5/4839* (2013.01); *A61B 5/4875* (2013.01); *A61B 5/7203* (2013.01); *A61B 5/7246* (2013.01); *A61B 5/7282* (2013.01); *A61B 8/08* (2013.01); *A61M 5/16831* (2013.01); *A61M 5/16836* (2013.01); *A61B 5/4878* (2013.01); *A61B 5/6824* (2013.01); *A61M 2205/3317* (2013.01); *F04C 2270/041* (2013.01)

(58) Field of Classification Search
CPC ... A61B 5/4878; A61B 5/6824; A61B 5/0537; A61B 5/4839; A61B 5/7203; A61B 5/7246; A61B 5/7282; A61M 5/16831; A61M 5/16836; A61M 2205/3317
See application file for complete search history.

(56) References Cited

U.S. PATENT DOCUMENTS

| | | | |
|---|---|---|---|
| 3,951,136 | A | 4/1976 | Wall |
| 4,010,749 | A | 3/1977 | Shaw |
| 4,240,445 | A | 12/1980 | Iskander et al. |
| 4,329,689 | A | 5/1982 | Yee |
| 4,378,808 | A | 4/1983 | Lichtenstein |
| 4,488,559 | A | 12/1984 | Iskander |
| 4,572,182 | A | 2/1986 | Royse |
| 4,575,705 | A | 3/1986 | Gotcher |
| 4,637,929 | A | 1/1987 | Quay |
| 4,641,659 | A | 2/1987 | Sepponen |
| 4,647,281 | A | 3/1987 | Carr |
| 4,648,869 | A | 3/1987 | Bobo, Jr. |
| 4,653,501 | A | 3/1987 | Cartmell et al. |
| 4,667,679 | A | 5/1987 | Sahota |
| 4,690,149 | A | 9/1987 | Ko |
| 4,816,019 | A | 3/1989 | Kamen |
| 4,819,648 | A * | 4/1989 | Ko .................. A61B 5/053 324/202 |
| 4,877,034 | A | 10/1989 | Atkins et al. |
| 4,923,442 | A | 5/1990 | Segall et al. |
| 4,959,050 | A | 9/1990 | Bobo, Jr. |
| 4,971,068 | A | 11/1990 | Sahi |
| 4,993,409 | A | 2/1991 | Grim |
| 4,997,055 | A | 3/1991 | Grady |
| 5,001,436 | A | 3/1991 | Scot et al. |
| 5,026,348 | A | 6/1991 | Venegas |
| 5,184,620 | A | 2/1993 | Cudahy et al. |
| 5,191,795 | A | 3/1993 | Fellingham et al. |
| 5,255,683 | A | 10/1993 | Monaghan |
| 5,334,141 | A | 8/1994 | Carr et al. |
| 5,479,927 | A | 1/1996 | Shmulewitz |
| 5,628,322 | A | 5/1997 | Mine |
| 5,685,305 | A | 11/1997 | Moonen et al. |
| 5,769,784 | A | 6/1998 | Barnett et al. |
| 5,840,026 | A | 11/1998 | Uber, III et al. |
| 5,861,019 | A | 1/1999 | Sun et al. |
| 5,947,910 | A | 9/1999 | Zimmet |
| 5,954,668 | A * | 9/1999 | Uber, III .......... A61M 5/16836 128/DIG. 13 |
| 5,957,950 | A | 9/1999 | Mockros et al. |
| 5,964,703 | A * | 10/1999 | Goodman ......... A61M 5/16836 600/382 |
| 5,995,863 | A | 11/1999 | Farace et al. |
| 6,026,173 | A | 2/2000 | Svenson et al. |
| 6,031,892 | A | 2/2000 | Karellas |
| 6,047,215 | A | 4/2000 | McClure et al. |
| 6,061,589 | A | 5/2000 | Bridges et al. |
| 6,233,476 | B1 | 5/2001 | Strommer et al. |
| 6,233,479 | B1 | 5/2001 | Haddad et al. |
| 6,251,073 | B1 | 6/2001 | Imran et al. |
| 6,263,226 | B1 | 7/2001 | Axelgaard et al. |
| 6,300,906 | B1 | 10/2001 | Rawnick et al. |
| 6,315,719 | B1 | 11/2001 | Rode et al. |
| 6,332,087 | B1 | 12/2001 | Svenson et al. |
| 6,367,023 | B2 * | 4/2002 | Kling .................. G06F 1/28 713/340 |
| 6,375,624 | B1 | 4/2002 | Uber, III et al. |
| 6,385,483 | B1 | 5/2002 | Uber, III et al. |
| 6,397,098 | B1 | 5/2002 | Uber, III et al. |
| 6,408,204 | B1 | 6/2002 | Hirschman |
| 6,415,170 | B1 | 7/2002 | Loutis et al. |
| 6,425,878 | B1 | 7/2002 | Shekalim |
| 6,454,711 | B1 | 9/2002 | Haddad et al. |
| 6,459,931 | B1 | 10/2002 | Hirschman |
| 6,487,428 | B1 | 11/2002 | Culver et al. |
| 6,520,930 | B2 | 2/2003 | Critchlow et al. |
| 6,587,428 | B2 | 7/2003 | Kuribayashi |
| 6,673,033 | B1 | 1/2004 | Sciulli et al. |
| 6,704,592 | B1 | 3/2004 | Reynolds et al. |
| 6,751,500 | B2 | 6/2004 | Hirschman |
| 6,970,735 | B2 | 11/2005 | Uber, III et al. |
| 7,047,058 | B1 | 5/2006 | Dvorsky et al. |
| 7,077,832 | B2 * | 7/2006 | Fleischmann ....... A61M 1/0088 602/48 |
| 7,122,012 | B2 | 10/2006 | Bouton et al. |
| 7,221,159 | B2 | 5/2007 | Griffiths et al. |
| 7,226,415 | B2 | 6/2007 | Haddad et al. |
| 7,283,860 | B2 | 10/2007 | Frazier et al. |
| 7,431,728 | B2 | 10/2008 | Gerry et al. |
| 7,457,804 | B2 | 11/2008 | Uber, III et al. |
| 7,532,953 | B2 * | 5/2009 | Vogel .................. A61M 1/0031 604/313 |
| 7,591,792 | B2 | 9/2009 | Bouton |
| 7,627,710 | B1 | 12/2009 | Todd et al. |
| 7,632,245 | B1 | 12/2009 | Cowan et al. |
| 7,674,244 | B2 | 3/2010 | Kalafut et al. |
| 7,713,239 | B2 | 5/2010 | Uber, III et al. |
| 7,937,134 | B2 | 5/2011 | Uber et al. |
| 7,996,381 | B2 | 8/2011 | Uber, III et al. |
| 8,055,328 | B2 | 11/2011 | Uber, III et al. |
| 8,096,957 | B2 | 1/2012 | Conquergood et al. |
| 8,160,679 | B2 | 4/2012 | Uber et al. |
| 8,182,444 | B2 | 5/2012 | Uber, III et al. |
| 8,192,397 | B2 | 6/2012 | Griffiths et al. |
| 8,295,920 | B2 | 10/2012 | Bouton et al. |
| 8,307,693 | B2 | 11/2012 | Uram et al. |
| 8,323,240 | B2 | 12/2012 | Wulfman et al. |
| 8,352,015 | B2 | 1/2013 | Bernstein et al. |
| 8,388,582 | B2 | 3/2013 | Eubanks et al. |
| 8,454,561 | B2 | 6/2013 | Uber, III et al. |
| 8,521,716 | B2 | 8/2013 | Uber, III et al. |
| 8,630,718 | B2 * | 1/2014 | Stahmann ........... A61N 1/0563 607/115 |
| 9,289,550 | B1 | 3/2016 | Dvorsky et al. |
| 2001/0044588 | A1 | 11/2001 | Mault |
| 2002/0040193 | A1 | 4/2002 | Hirschman |
| 2002/0123674 | A1 | 9/2002 | Plicchi et al. |
| 2002/0172323 | A1 | 11/2002 | Karellas et al. |
| 2003/0004433 | A1 | 1/2003 | Hirschman |
| 2003/0036674 | A1 | 2/2003 | Bouton |
| 2003/0036713 | A1 | 2/2003 | Bouton et al. |

(56) References Cited

U.S. PATENT DOCUMENTS

| | | | |
|---|---|---|---|
| 2003/0120170 A1 | 6/2003 | Zhu et al. | |
| 2004/0086734 A1* | 5/2004 | Janssens | B32B 27/20 |
| | | | 428/482 |
| 2004/0162488 A1 | 8/2004 | Uber, III et al. | |
| 2004/0225255 A1* | 11/2004 | Ono | A61B 5/0059 |
| | | | 604/65 |
| 2005/0015009 A1* | 1/2005 | Mourad | A61B 5/031 |
| | | | 600/438 |
| 2005/0073424 A1 | 4/2005 | Ruoss et al. | |
| 2005/0234428 A1* | 10/2005 | Spohn | A61M 5/007 |
| | | | 604/533 |
| 2006/0025897 A1* | 2/2006 | Shostak | B60C 23/005 |
| | | | 701/1 |
| 2006/0122497 A1 | 6/2006 | Glossop | |
| 2006/0135884 A1* | 6/2006 | Hack | A61B 5/05 |
| | | | 600/547 |
| 2006/0211970 A1 | 9/2006 | Sciulli | |
| 2006/0213234 A1* | 9/2006 | Gladfelter | D03D 1/0047 |
| | | | 66/190 |
| 2006/0213249 A1 | 9/2006 | Uram et al. | |
| 2007/0056871 A1 | 3/2007 | Griffiths et al. | |
| 2007/0123770 A1 | 5/2007 | Bouton et al. | |
| 2007/0225601 A1 | 9/2007 | Uber, III et al. | |
| 2007/0225637 A1 | 9/2007 | Ono et al. | |
| 2007/0244428 A1 | 10/2007 | Uram et al. | |
| 2007/0276327 A1* | 11/2007 | Kalafut | A61M 5/14546 |
| | | | 604/131 |
| 2007/0282198 A1 | 12/2007 | Uber, III et al. | |
| 2007/0282199 A1 | 12/2007 | Uber, III et al. | |
| 2008/0058680 A1 | 3/2008 | Lee et al. | |
| 2008/0058758 A1 | 3/2008 | Ranchod et al. | |
| 2008/0097339 A1 | 4/2008 | Ranchod et al. | |
| 2008/0166292 A1 | 7/2008 | Levin et al. | |
| 2008/0167900 A1 | 7/2008 | Ranchod | |
| 2008/0195060 A1 | 8/2008 | Roger et al. | |
| 2008/0294096 A1 | 11/2008 | Uber, III et al. | |
| 2008/0319285 A1 | 12/2008 | Hancock | |
| 2009/0015353 A1 | 1/2009 | Rofougaran | |
| 2009/0070342 A1 | 3/2009 | Uber, III et al. | |
| 2009/0177050 A1 | 7/2009 | Griffiths et al. | |
| 2009/0247866 A1 | 10/2009 | Uber, III et al. | |
| 2009/0276327 A1 | 11/2009 | Malik | |
| 2009/0299175 A1 | 12/2009 | Bernstein et al. | |
| 2009/0326370 A1 | 12/2009 | Uber, III et al. | |
| 2010/0049004 A1* | 2/2010 | Edman | A61B 5/1118 |
| | | | 600/300 |
| 2010/0113887 A1 | 5/2010 | Kalafut et al. | |
| 2010/0114064 A1 | 5/2010 | Kalafut et al. | |
| 2010/0160786 A1 | 6/2010 | Nordgren et al. | |
| 2010/0174179 A1 | 7/2010 | Persson et al. | |
| 2010/0185040 A1 | 7/2010 | Uber, III et al. | |
| 2010/0198141 A1 | 8/2010 | Laitenberger et al. | |
| 2010/0256462 A1 | 10/2010 | Rappaport et al. | |
| 2011/0002802 A1 | 1/2011 | Capone et al. | |
| 2011/0130800 A1 | 6/2011 | Weinstein et al. | |
| 2011/0257522 A1 | 10/2011 | Berard-Andersen et al. | |
| 2012/0019386 A1 | 1/2012 | Doraiswami et al. | |
| 2013/0062528 A1 | 3/2013 | Hyde et al. | |
| 2013/0079581 A1 | 3/2013 | Agamaite et al. | |
| 2013/0123567 A1 | 5/2013 | Agamaite et al. | |
| 2013/0123614 A1 | 5/2013 | Bernstein et al. | |
| 2013/0131585 A1 | 5/2013 | Eubanks et al. | |
| 2013/0190646 A1 | 7/2013 | Weinstein et al. | |
| 2013/0231550 A1 | 9/2013 | Weinstein et al. | |
| 2013/0253254 A1 | 9/2013 | Uber, III et al. | |
| 2013/0255390 A1 | 10/2013 | Riley et al. | |
| 2013/0274599 A1 | 10/2013 | Bouton et al. | |
| 2013/0331634 A1 | 12/2013 | Kaintz et al. | |
| 2013/0331635 A1 | 12/2013 | Hoffman et al. | |
| 2013/0331810 A1 | 12/2013 | Bazala et al. | |
| 2013/0345676 A1 | 12/2013 | Wulfman et al. | |
| 2014/0046295 A1 | 2/2014 | Uber, III et al. | |
| 2014/0228686 A1 | 8/2014 | Bouton | |
| 2020/0315492 A1 | 10/2020 | Bouton | |

FOREIGN PATENT DOCUMENTS

| | | |
|---|---|---|
| DE | 4007587 | 9/1991 |
| EP | 1472973 | 11/2004 |
| EP | 1647306 | 4/2006 |
| EP | 2455402 | 5/2012 |
| EP | 2526857 | 11/2012 |
| EP | 2750594 | 7/2014 |
| EP | 2750595 | 7/2014 |
| GB | 2251080 | 6/1992 |
| JP | 1157001 | 3/1999 |
| JP | 2007509353 | 4/2007 |
| WO | 9926685 | 6/1999 |
| WO | 9926686 | 6/1999 |
| WO | 9929356 | 6/1999 |
| WO | 0108729 | 2/2001 |
| WO | 2003000972 A1 | 1/2003 |
| WO | 03009752 | 2/2003 |
| WO | 03063680 | 8/2003 |
| WO | 2004036467 | 4/2004 |
| WO | 2005043100 | 5/2005 |
| WO | 03009753 | 2/2006 |
| WO | 2008100670 | 8/2008 |
| WO | 2009009753 A1 | 1/2009 |
| WO | 20100146372 | 12/2010 |
| WO | 2011067623 | 6/2011 |
| WO | 2011067685 | 6/2011 |
| WO | 2012011065 | 1/2012 |
| WO | 2012011066 | 1/2012 |
| WO | 2012059929 | 5/2012 |
| WO | 2013033162 | 3/2013 |
| WO | 2013033166 | 3/2013 |
| WO | 2013033174 | 3/2013 |
| WO | 2013093923 | 6/2013 |
| WO | 2013147799 | 10/2013 |

OTHER PUBLICATIONS

Chad E. Bouton; U.S. Appl. No. 14/241,179, filed Mar. 11, 2014 entitled Wireless and Power-Source-Free Extravasation and Infiltration Detection Sensor; United States Patent and Trademark Office; Alexandria, VA (National Stage of PCT/US2012/052801 filed Aug. 29, 2012).

De la Hera, German; International Search Report and Written Opinion; International Application No. PCT/US2012/052796; dated Dec. 10, 2012; European Patent Office.

De la Hera, German; International Search Report and Written Opinion; International Application No. PCT/US2012/052801; dated Dec. 19, 2012; European Patent Office.

De la Hera, German; International Search Report and Written Opinion; International Application No. PCT/US2012/052813; dated Dec. 7, 2012; European Patent Office.

Shaeffer, James et al.; Detection of Extravasation of Antineoplastic Drugs by Microwave Radiometry; Cancer Letter, 31; pp. 284-291; 1986; Elsevier Scientific Publishers Ireland Ltd.

Sukamto, Lin M. et al.; MMIC Receiver for Water-Vapor Radiometer; NASA Tech Briefs; p. 34; Sep. 1993.

Arkin, H. et al.; Recent Developments in Modeling Heat Transfer in Blood Perfused Tissues; IEEE Transactions on Biomedical Engineering; vol. 41, No. 2; pp. 97-107; Feb. 1994.

Harris, Thomas S. et al.; Infusion Line Model for the Detection of Infiltration Extravasation, and other Fluid Flow Faults; IEEE Transactions on Biomedical Engineering; vol. 40, No. 2; pp. 154-162; Feb. 1993.

Montreuil, Jean et al.; Multiangle Method for Temperature Measurement of Biological Tissues by Microwave Radiometry; IEEE Transactions on Microwave Theory and Techniques; vol. 39, No. 7; pp. 1235-1238; Jul. 1991.

Lin, James C. et al.; Microwave Imaging of Cerebral Edema; Proceedings of the IEEE; vol. 70, No. 5; pp. 523-524; May 1982.

Kramer, Gerhard G. et al.; Dielectric Measurement of Cerebral Water Content Using a Network Analyzer; Neurological Research; vol. 14, No. 3; pp. 255-258; Sep. 1992.

(56) References Cited

OTHER PUBLICATIONS

Ling, Geoffrey S.F. et al.; Diagnosis of Subdural and Intraparenchymal Intracranial Hemorrhage Using a Microwave Based Detector; Digitization of the Battlespace V and Battlefield Biomedical Technologies II; vol. 4037; pp. 212-217; Apr. 24, 2000.
Behari, J. et al.; Dielectric Permittivity of Biological Tissues in the Microwave Frequency Range; Proceedings of the SPIE—The International Society for Optical Engineering, Advanced Microwave and Millimeter-Wave Detectors; vol. 2275; pp. 301-308; San Diego, CA; Jul. 25-26, 1994.
Andreuccetti, D. et al.; High Permittivity Patch Radiator for Single and Multi-Element Hyperthermia Applicators; IEEE Transactions on Biomedical Engineering; vol. 40, No. 7; pp. 711-715; IEEE Inc.; New York; Jul. 1, 1993.
Lee, Eric R. et al.; Body Conformable 915 MHz Microstrip Array Applicators for Large Surface Area Hyperthermia; IEEE Transactions on Biomedical Engineering; vol. 39, No. 5; pp. 470-438; IEEE Inc., New York; May 1, 1992.
Jameson, P.; International Search Report; Application No. PCT/US00/20112; dated Oct. 17, 2000; European Patent Office.
Van Dooren, G.; International Search Report; Application No. PCT/US02/23877; dated Feb. 6, 2003; European Patent Office.
Beitner, M.; International Search Report; Application No. PCT/US02/23925; dated Jan. 15, 2003; European Patent Office.
P.B. James and R.W. Galloway; The Ultrasonic Blood Velocity Detector as an Aid to Arteriography; Br J Radiol; Oct. 1971; 44:743-746.
European Search Report for EP12005361 dated Mar. 6, 2013.
Bouton, Chad E.: Final Office Action; U.S. Appl. No. 13/620,310; dated Jan. 6, 2014; United States Patent and Trademark Office; Alexandria, VA.
Supplementary European Search Report for EP04796177 dated May 11, 2010.
Partial European Search Report for EP12005361 dated Nov. 2, 2012.
Kent: "Hand-Held Instrument for Fat/Water Determination in Whole Fish"; 1993; at http://distell.com/products/prd-fish-fatmeter/technical-data/ffm-research-paper.
Birnbaum et al.: "Extravasation Detection Accessory: Clinical Evaluation in 500 Patients"; 1999; Radiology 212:431-438.
"Value of Multi-Detector Array CT in the Assessment of Portal Hypertension"; Portal Hypertension: Diagnostic Imaging and Imaging-Guided Therapy (Medical Radiology/Diagnostic Imaging).; Ed. Plinio Rossi. 1st ed.; Springer; 2000; p. 111.
International Preliminary Report on Patentability and Written Opinion dated Oct. 5, 2005 for PCT/US2004/35135.
International Search Report for PCT/US2004/035135 dated Oct. 5, 2005.
Chad E. Bouton; U.S. Appl. No. 14/241,171, filed Mar. 11, 2014 entitled Distributed Extravasation Detection Sytem; United States Patent and Trademark Office; Alexandria, VA (National Stage of PCT/US2012/052796 filed Aug. 29, 2012).
Carr, Kenneth L; Use of Gallium Arsenide in Medical Applications: Microwave Medical Systems, Inc.; GaAs IC Symposium; pp. 10-13; 1999 IEEE.
Shaeffer, James et al.; Early Detection of Extravasation of Radiographic Contrast Medium; Radiology; pp. 141-144; Jul. 1992.
Gupta, Vani, First Office Action, U.S. Appl. No. 14/241,171; dated Sep. 10, 2015; United States Patent and Trademark Office, Alexandria, VA.
Gupta, Vani; Office Action; U.S. Appl. No. 14/241,179; dated Dec. 9, 2015; United States Patent and Trademark Office; Alexandria, Virginia.
Gupta, Vani; Office Action; U.S. Appl. No. 14/241,171; dated Jun. 17, 2016; United States Patent and Trademark Office, Alexandria, VA.
Gupta, Vani; Office Action; U.S. Appl. No. 14/241,179; dated Jun. 29, 2016; United States Patent and Trademark Office, Alexandria, VA.
Gupta, Vani; Office Action; U.S. Appl. No. 14/241,171; dated Dec. 16, 2016; United States Patent and Trademark Office, Alexandria, VA.
Gupta, Vani; Office U.S. Appl. No. 14/241,179; dated Oct. 11, 2016; United States Patent and Trademark Office, Alexandria, VA.
Gupta, Vani; Office Action; U.S. Appl. No. 14/241,179; dated May 22, 2017; United States Patent and Trademark Office, Alexandria, Virginia.
Gupta, Vani; Office Action; U.S. Appl. No. 14/241,171; dated Jul. 25, 2017; United States Patent and Trademark Office, Alexandria, Virginia.
Gupta, Vani; Final Office Action; U.S. Appl. No. 14/241,179; dated May 18, 2018; United States Patent and Trademark Office; Alexandria, VA.
Gupta, Vani; Final Office Action; U.S. Appl. No. 14/241,171; dated May 29, 2018; United States Patent and Trademark Office; Alexandria, VA.
IP, Jason M.; Final Office Action; U.S. Appl. No. 13/620,310; dated Mar. 5, 2018; United States Patent and Trademark Office; Alexandria, VA.
IP, Jason M.; Office Action; U.S. Appl. No. 13/620,310; dated Jul. 27, 2017; United States Patent and Trademark Office; Alexandria, VA.
IP, Jason M.; Final Office Action; U.S. Appl. No. 13/620,310; dated Jun. 14, 2016; United States Patent and Trademark Office; Alexandria, VA.
IP, Jason M.; Advisory Action; U.S. Appl. No. 13/620,310; dated May 5, 2016; United States Patent and Trademark Office; Alexandria, VA.
IP, Jason M.; Final Office Action; U.S. Appl. No. 13/620,310; dated Feb. 5, 2016; United States Patent and Trademark Office; Alexandria, VA.
IP, Jason M.; Office Action; U.S. Appl. No. 13/620,310; dated May 29, 2015; United States Patent and Trademark Office; Alexandria, VA.
IP, Jason M.; Final Office Action; U.S. Appl. No. 13/620,310; dated Aug. 7, 2014; United States Patent and Trademark Office; Alexandria, VA.
IP, Jason M.; Office Action; U.S. Appl. No. 13/620,310; dated Apr. 23, 2014; United States Patent and Trademark Office; Alexandria, VA.
IP, Jason M.; Office Action; U.S. Appl. No. 13/620,310; dated Sep. 9, 2013; United States Patent and Trademark Office; Alexandria, VA.
Bor, Helene Catherine; Notice of Allowance; U.S. Appl. No. 11/385,448; dated Nov. 20, 2015; United States Patent and Trademark Office; Alexandria, VA.
Bor, Helene Catherine; Final Office Action; U.S. Appl. No. 11/385,448; dated Jun. 3, 2015; United States Patent and Trademark Office; Alexandria, VA.
Bor, Helene Catherine; Office Action; U.S. Appl. No. 11/385,448; dated Sep. 30, 2014; United States Patent and Trademark Office; Alexandria, VA.
Bor, Helene Catherine; Office Action; U.S. Appl. No. 11/385,448; dated Jan. 6, 2014; United States Patent and Trademark Office; Alexandria, VA.
Bor, Helene Catherine; Final Office Action; U.S. Appl. No. 11/385,448; dated Jul. 18, 2013; United States Patent and Trademark Office; Alexandria, VA.
Bor, Helene Catherine; Office Action; U.S. Appl. No. 11/385,448; dated Dec. 28, 2012; United States Patent and Trademark Office; Alexandria, VA.
Bor, Helene Catherine; Advisory Action; U.S. Appl. No. 11/385,448; dated Aug. 29, 2011; United States Patent and Trademark Office; Alexandria, VA.
Fontenot, Nigel Rai; Final Office Action; U.S. Appl. No. 11/385,448; dated Mar. 28, 2011; United States Patent and Trademark Office; Alexandria, VA.
Fontenot, Nigel Rai; Office Action; U.S. Appl. No. 11/385,448; dated Dec. 3, 2010; United States Patent and Trademark Office; Alexandria, VA.

(56) References Cited

OTHER PUBLICATIONS

Fontenot, Nigel Rai; Final Office Action; U.S. Appl. No. 11/385,448; dated Feb. 24, 2010; United States Patent and Trademark Office; Alexandria, VA.
Fontenot, Nigel Rai; Office Action; U.S. Appl. No. 11/385,448; dated Sep. 30, 2009; United States Patent and Trademark Office; Alexandria, VA.
Fontenot, Nigel Rai; Final Office Action; U.S. Appl. No. 11/385,448; dated May 13, 2009; United States Patent and Trademark Office; Alexandria, VA.
Fontenot, Nigel Rai; Office Action; U.S. Appl. No. 11/385,448; dated Nov. 13, 2008; United States Patent and Trademark Office; Alexandria, VA.
Gupta, Vani; Office Action; U.S. Appl. No. 14/241,171; dated Mar. 20, 2019; U.S. Patent and Trademark Office; Alexandria; VA.
Gupta, Vani; Office Action; U.S. Appl. No. 14/241,179; dated Nov. 28, 2018; U.S. Patent and Trademark Office; Alexandria; VA.
De la Hera, Germán; Examination Report; European Patent Application No. 12772147.0; dated Oct. 8, 2018; European Patent Office, Munich, Germany.
De la Hera, German; Office Action; European Patent Application No. 12759562.7; dated Oct. 5, 2018; European Patent Office, Munich, Germany.
Serkan, Akar; Notice of Allowance; U.S. Appl. No. 14/241,179; dated Aug. 13, 2019; United States Patent and Trademark Office; Alexandria, VA.
Akar, Serkan; Final Office Action; U.S. Appl. No. 14/241,171; dated Aug. 28, 2019; U.S. Patent and Trademark Office; Alexandria, VA.
EPO Examination Report; European Patent Application No. 12759562.7; dated Feb. 4, 2020; European Patent Office; Munich, Germany.
Notice of Allowance and Fees Due; U.S. Appl. No. 14/241,171, filed Dec. 1, 2020; United States Patent and Trademark Office; Alexandria, VA.
Chad E. Bouton; Related U.S. continuation U.S. Appl. No. 17/072,428, filed Oct. 16, 2020 entitled Extravasation and Infiltration Detection Device.
International Preliminary Report on Patentability and Written Opinion of the International Searching Authority dated Mar. 4, 2014; International Application No. PCT/US2012/052813; International Bureau of WIPO; Geneva, Switzerland.
Communication under Rule 71(3) EPC Intention to grant dated Mar. 17, 2020; European Application No. 12772147; European Patent Office; Munich, Germany.
Chad E. Bouton; Related U.S. Continuation U.S. Appl. No. 17/249,321, filed Feb. 26, 2021 entitled "Distributed Extravasation Detection System"; United States Patent and Trademark Office; Alexandria, Virginia.

* cited by examiner

US 11,234,608 B2

EXTRAVASATION AND INFILTRATION DETECTION DEVICE WITH FLUID GUIDE PROVIDED ON A SUBSTRATE OF THE DETECTION DEVICE TO ADJUST FLUID RATE BASED ON DETECTION SIGNAL

TECHNICAL FIELD

The present invention relates generally to the detection of fluids in tissue, and, more particularly, to apparatuses, systems and methods for detection of changed, elevated or abnormal fluid levels in tissue.

BACKGROUND ART

Changed, elevated or abnormal fluid levels in living tissue can result from a number of physiological conditions. For example, edema is an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions.

Moreover, bleeding (hemorrhage) can cause blood to collect and clot (hematoma). Hematomas can, for example, occur beneath the outermost of three membranes that cover the brain (meninges) as a result of a head injury. There are two types of cranial subdural hematomas. An acute subdural hematoma occurs soon after a severe head injury. A chronic subdural hematoma is a complication that may develop weeks after a head injury. Such a head injury may have been so minor that the patient does not remember it. An epidural hematoma is a traumatic accumulation of blood between the inner table of the skull and the stripped-off dural membrane. The inciting event often is a focused blow to the head. It is often difficult to detect hematomas, particularly when the hematoma occurs well after the time of an injury.

In addition to accumulation of body fluids, elevated fluid levels in tissue can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and NMR/MRI (Nuclear Magnetic Resonance/Magnetic Resonance Imaging) have been developed.

Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modern procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

In U.S. Pat. No. 7,122,012 to Bouton, et al., issued Oct. 17, 2006, which is hereby incorporated by reference in its entirety, a method was disclosed for detecting a change in the level of fluid in tissue in a first area of a body. Steps included applying electromagnetic energy, preferably in the frequency range of approximately 300 MHz to approximately 30 GHz, to a first volume of the body; measuring a resultant or returned signal; comparing the signal to a reference signal to determine if the fluid level in the tissue has changed. In one embodiment, the method detected changes in the level of fluid in tissue of a body by applying electromagnetic energy to a first volume of the body over a period of time; measuring a resultant signal or a signal returned from the tissue; and comparing the signal to a reference signal to determine if a level of fluid in the tissue has changed during the period of time.

DISCLOSURE OF INVENTION

The following presents a simplified summary. This summary is not an extensive overview and is intended to neither identify key or critical elements nor delineate the scope of such aspects. Its purpose is to present some concepts of the described features in a simplified form as a prelude to the more detailed description that is presented later.

In accordance with one or more aspects and embodiments, and the corresponding disclosures thereof, various features of the invention are described in connection with an integrated device and/or a system for detecting extravasation or infiltration. Incorporating more of the functionality into a device worn by a patient undergoing a fluid injection, infusion, or Intravenous (IV) drip enables more mobility.

In one aspect, the present disclosure provides an apparatus for detecting extravasation or infiltration. A transmitter is positioned to direct power into a body portion. A sensor is positioned to receive the power transmitted through the body portion. A substrate is attachable to an outer surface of the body portion and supports the transmitter, the sensor and one of a signal processor and the power supply. The signal processor is coupled to the transmitter and the sensor for detecting a change in a fluid level in the body portion from extravasation or infiltration based on the power received by the sensor. Advantageously, a power supply is coupled to the transmitter and the sensor. An indicator is responsive to the signal processor to indicate a detected change in a fluid level in the body portion from extravasation or infiltration.

In some embodiments, the substrate supports the signal processor, the power supply, and the indicator.

In some embodiments, a fluid guiding component is positioned on the substrate.

In further embodiments, a marked transparent substrate is provided to expose a vascular structure of the body portion.

In yet further embodiments, the transmitter comprises a Radio Frequency (RF) transmitter and the sensor comprises an RF sensor. In a particularly suitable embodiment, an RF absorbing layer is externally disposed over at least a portion of the transmitter, sensor and substrate.

In yet other embodiments, the transmitter comprises an ultrasonic transmitter and the sensor comprises an ultrasonic sensor. In a suitable embodiment, the signal processor is further for detecting the change in the fluid level in the body portion from extravasation or infiltration based upon changes in amplitude and phase for propagation of the directed power.

In some embodiments, the indicator indicates a selected one of a deactivated state, a baseline state, and a fluid detected state.

In some embodiments, the indicator may indicate a change in received power from a baseline received power, and the substrate may comprise a flexible material for physical palpation.

In some embodiments, the substrate comprises wound dressing material.

In a second aspect, there is provided a device for detecting extravasation or infiltration. The device may comprise an apparatus having any of the features described in relation to the first aspect of the invention. In one embodiment the device of this aspect of the invention may comprise a transmitter positioned to direct power into a body portion. Furthermore, a sensor may be positioned to receive the power transmitted through the body portion. A signal processor may be coupled to the transmitter and the sensor for detecting a change in a fluid level in the body portion from extravasation or infiltration based on the power received by the sensor. A power supply may conveniently be coupled to the transmitter and the sensor. An indicator may be provided which is responsive to the signal processor to indicate a detected change in a fluid level in the body portion from extravasation or infiltration. The device may further comprise a substrate attachable to an outer surface of the body portion, in use, and supporting one or more and conveniently all of the transmitter, the sensor, the signal processor, the power supply, and the indicator. A fluid guiding component may be positioned on the substrate. The transmitter and sensor are suitably positioned relative to the fluid guiding component to detect fluid extravasation or infiltration arising from fluid insertion to a vascular structure.

In a third aspect, the present disclosure provides a method for detecting extravasation or infiltration. The method may suitably comprise the use of a device, apparatus or system of the invention. In some embodiments, the method detects extravasation or infiltration, comprising: inserting a fluid injection conduit into a vascular structure in a body portion; activating detection circuitry attached to a substrate to obtain a baseline measurement for a power waveform transmitted into the body portion; injecting fluid into the vascular structure via the fluid injection conduit; detecting a change in the power waveform by the detection circuitry due to extravasation or infiltration; and determining a duty cycle for the detection circuitry required to effectively monitor the type of fluid being injected into the body portion and to minimize power consumption.

In a fourth aspect of the present invention, an apparatus is provided for detecting a change in a body portion, comprising: a transmitter positioned to direct power into a body portion; a sensor positioned to receive the power transmitted through the body portion; a signal processor coupled to the transmitter and the sensor for detecting a change in the body portion based on the power received by the sensor; a power supply coupled to the transmitter and the sensor; a substrate attachable to the body portion and supporting the transmitter, the sensor, and at least one of the signal processor and the power supply; and an indicator provided on the substrate responsive to the signal processor to indicate a detected change in the body portion. In some embodiments, the apparatus for detecting a change in a body portion comprises an apparatus having any of the features described in relation to the first and/or second aspect of the invention.

The substrate may support the signal processor and the power supply.

A fluid guiding component may be positioned on the substrate.

The indicator on the substrate in any aspect and embodiment of the invention may comprise a light-emitting diode (LED) lamp or other light or speaker for generating a tone. In this fourth aspect, the indicator may be actuated to generate a light alert signal indicative of a detected change in a body portion and/or a tone or other sound which is activated to generate an audible alert signal indicative of a detected change in a body portion.

The signal processor may detect a change in a body portion comprising a change in fluid level in the body portion. In one embodiment, the change in fluid level in the body portion may result from extravasation or infiltration. Further, the signal processor, coupled to the transmitter and the sensor, may detect a change in the body portion based on the power received by the sensor, using known processing techniques, resulting from peripheral edema (i.e., fluid in arms/legs), edema around the heart, wherein peripheral edema and edema around the heart are both indicative of congestive heart failure, fluid in the lungs, and blood accumulation under the skull (subcranial hematoma), which may be useful to detect early in suspected concussions or traumatic brain injuries.

To the accomplishment of the foregoing and related ends, one or more aspects or embodiments comprise the features hereinafter fully described and particularly pointed out in the claims. The following description and the annexed drawings set forth in detail certain illustrative aspects and are indicative of but a few of the various ways in which the principles of the aspects may be employed. Other advantages and novel features will become apparent from the following detailed description when considered in conjunction with the drawings and the disclosed aspects are intended to include all such aspects and their equivalents.

BRIEF DESCRIPTION OF DRAWINGS

The disclosed aspects will hereinafter be described in conjunction with the appended drawings, provided to illustrate and not to limit the disclosed aspects, wherein like designations denote like elements, and in which.

MODES FOR CARRYING OUT THE INVENTION

A device is provided for detecting extravasation or infiltration. A transmitter is positioned to direct power into a body portion. A sensor is positioned to receive the power transmitted through the body portion. A substrate is attachable to an outer surface of the body portion and supports the transmitter and the sensor. A signal processor is coupled to the transmitter and the sensor for detecting a change in a fluid level in the body portion from extravasation or infiltration based on the power received by the sensor. More particularly and in the illustrated embodiment, the signal processor detects a change in fluid level based on a comparison between a current power received by the sensor and a baseline power received by the sensor earlier in time. A power supply is coupled to the transmitter and the sensor. An indicator is responsive to the signal processor to indicate a detected change in a fluid level in the body portion from extravasation or infiltration.

An integrated substrate and sensor assembly for catheter extravasation detection applications can save time. In many cases, the nurse or technologist has a short time window to prepare a patient for intravenous (IV) therapy or a contrast injection such as for a CT/MRI (Computerized Tomography/Magnetic Resonance Imaging) examination. For another example, correct placement of the transmitters and sensors is necessary for correctly detecting an extravasation or infiltration. Integrating the components maintains correct placement. In some implementations, a patient can be ambulatory, mobile, or at least alert, such as when receiving a long duration infusion or IV drip. The patient may be the one that serves as the primary person for monitoring an indication for extravasation or infiltration. An integrated indicator can thus alert the patient, ensuring timely intervention.

The substrate may be disposable and should be made of a material that has a low attenuation factor with respect to the sensor's power. For example with the Permittivity Sensor technology (see, for example, U.S. Pat. No. 7,122,012), radio-frequency energy is used, and therefore a material with a low RF dissipation factor (or imaginary permittivity value) would allow transmission of the radio-frequency energy into the tissue for proper sensing of fluid accumulation, IV infiltration, or extravasation.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Figure 1:
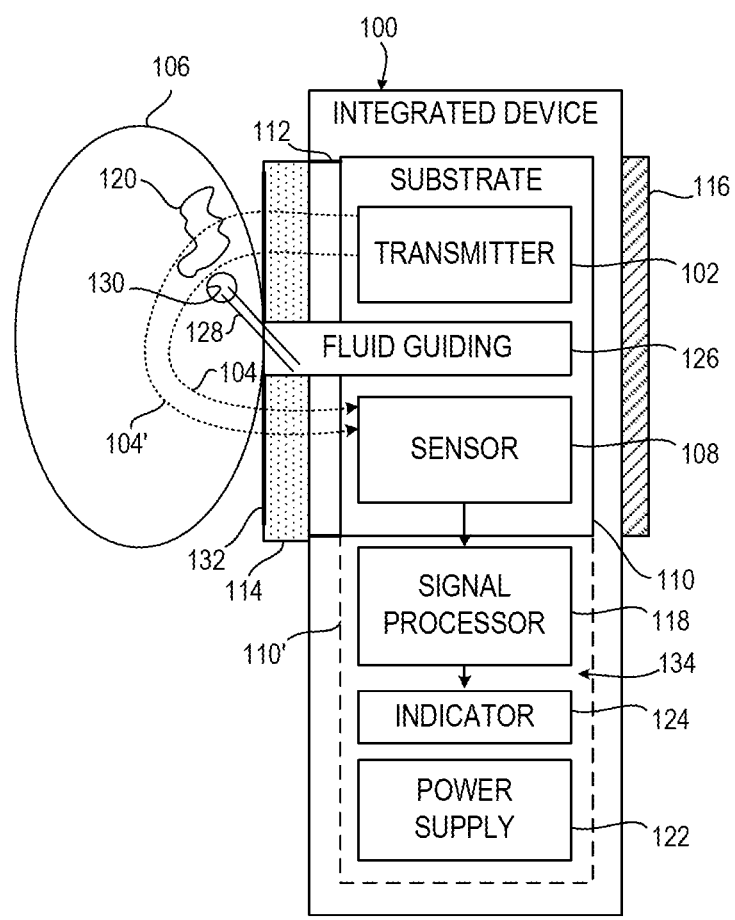
FIG. 1 is a schematic block diagram of an integrated device for detecting a change in a fluid level in tissue, according to one aspect.
Figure 2:
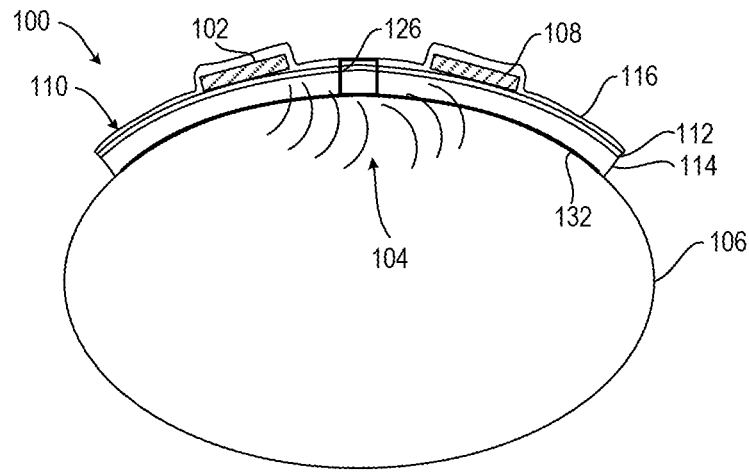
FIG. 2 is a cross sectional view of the integrated device of FIG. 1.
Figure 3:
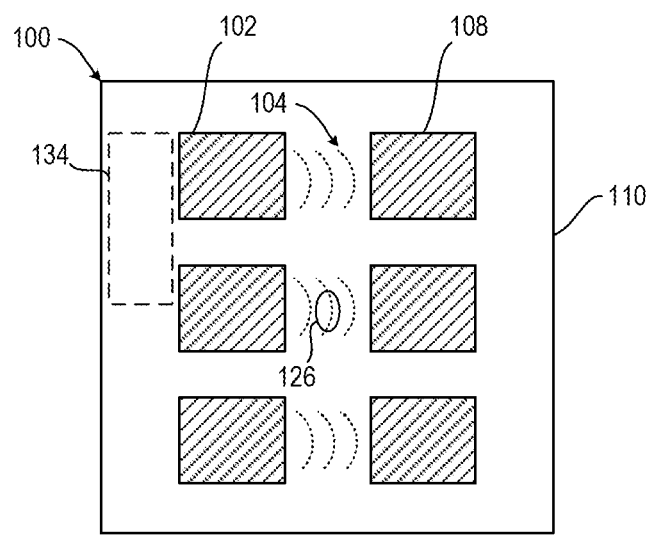
FIG. 3 is a top view of the integrated device of FIG. 1.

In FIGS. 1-3, the present disclosure provides an apparatus, depicted as an integrated device 100, for detecting extravasation or infiltration. One or more transmitters 102 are positioned to direct power as depicted at 104 (e.g., during a baseline operation prior to fluid being provided to a patient) or 104' (e.g., during a patient measurement operation while fluid is being injected into a patient) into a body portion 106. One or more sensors 108 are positioned to receive the power after passing through the body portion 106. A substrate 110 is attachable to an outer surface of the body portion 106 and supports at least the transmitters 102 and the sensors 108.

In one aspect, the substrate 110 may comprise a structural layer 112 for attaching components and for receiving fastening members, a dressing layer 114 such as gauze underlying the structural layer 112 for contacting the body portion 106, and an isolating layer 116 over top of the structural layer 112. In one aspect for a transmitter 102 and sensor 108 that use RF power, the isolating layer can serve not only to hold the transmitters 102 and sensors 108 in place but can contain iron powder filler to reduce stray RF. The dressing layer 114 can have a low RF attenuation factor.

With particular reference to FIG. 1, a signal processor 118 is coupled to the transmitters 102 and the sensor 108 for detecting a change in a fluid level in the body portion from extravasation or infiltration based on a change in the power 104 or 104' received by the sensor 108, i.e., a change of a current power relative to a baseline power. For example, at a baseline time, the power 104 encounters a baseline condition of fluid level. At a subsequent current time, i.e., during a patient measurement operation while a fluid is being injected into the patient, the power 104' may encounter a change, depicted at 120 as an increase (extravasation, infiltration, etc.) in fluid, typically resulting in a reduced amount of power 104' being received by the sensors 108 as power is absorbed by the fluid. A power supply 122 is coupled to the transmitters 102 and the sensors 108. An indicator 124 is responsive to the signal processor 118 to indicate a detected change in a fluid level in the body portion 106 from extravasation or infiltration.

In one exemplary aspect, a substrate 110 further supports one or more, or all of the signal processor 118, the power supply 122, and the indicator 124. In a preferred embodiment, the substrate 110 supports the transmitters 102, the sensors 108, the signal processor 118, the power supply 122 and the indicator 124, such that the integrated device 100 comprises a small, stand-alone device, which can be fully supported by a patient. With this stand-alone, integrated device 100 of the present invention, there are no cables. Devices having one or more cables extending to a processor or the like may result in a cable being accidentally pulled, causing a corresponding transmitter and/or sensor being displaced on a patient. As noted above, typically, an extravasation, infiltration results in a reduced amount of power 104' being received by the sensors 108. Hence, if a cable causes a transmitter and/or sensor to be displaced on a patient, this may result in a processor incorrectly determining that an extravasation, infiltration condition exists. This risk of error is reduced or eliminated with the integrated device 100 of the present invention.

In another exemplary aspect, a fluid guiding component 126 is positioned on the substrate 110. The transmitters 102 and the sensors 108 are positioned relative to the fluid guiding component 126 to detect fluid extravasation or infiltration arising from fluid insertion to a patient vascular structure 130 via a needle or catheter 128 associated with the fluid guiding component 126.

With particular reference to FIGS. 2-3, the structural layer 112 of the substrate 110 of the integrated device 100 may comprise a layer of a flexible material to accommodate various anatomy topologies while providing an adhesive border 132 to hold the dressing layer 114 in place. The dressing layer 114 can be compatible with wounds/burns or a thin membrane that holds the needle or catheter 128 in place. In an additional exemplary aspect, a marked transparent substrate exposes the vascular structure 130 of the body portion 106 and facilitates alignment of the integrated device 100. The structural layer 112 can hold integrated circuitry 134, comprising the transmitters 102, the sensors 108, the signal processor 118, the power supply 122 and the indicator 124, for extravasation or infiltration detection.

The one or more transmitters 102 may comprise one or more transmitting antennas and the one or more sensors 108 may comprise one or more receiving antennas. In an exemplary aspect, the transmitting and receiving antennas are microstrip (or often called planar) type antennas, allowing construction of a thinner type integrated device 100. As noted above, the sensors 108 may be located in the layer 112 above the protective gauze of the dressing. In this location, the sensors 108 can detect fluid accumulation in the tissue below or the dressing/gauze. After a baseline measurement is made, fluid accumulation or increase at a wound site can be indicative of an infection starting or worsening.

Thus, in one aspect, the present disclosure provides the integrated device 100 for detecting extravasation or infiltration. The transmitter(s) 102 is positioned to direct power 104 into the body portion 106. The sensor(s) 108 is positioned to receive the power 104 transmitted through the body portion 106. The signal processor 118 is coupled to the transmitter(s) 102 and the sensor(s) 108 for detecting a change in a fluid level in the body portion 106 from extravasation or infiltration based on a change in a current power 104, 104' received by the sensor 108 relative to baseline power level received by the sensor 108 earlier in time. The power supply 122 is coupled to the transmitter 102 and the sensor 108. The indicator 124 is responsive to the signal processor 118 to indicate a detected change in a fluid level in the body portion 106 from extravasation or infiltration. The substrate 110 is attachable to an outer surface of the body portion 106 and, as discussed above, may support the transmitter(s) 102, the sensor(s) 108, the signal processor 118, the power supply 122, and the indicator 124. The fluid guiding component 126 is positioned on the substrate 110. The transmitter(s) 102 and the sensor(s) 108 are positioned relative to the fluid guiding component 126 to detect fluid extravasation or infiltration arising from fluid insertion to the patient vascular structure 130.

Figure 4:
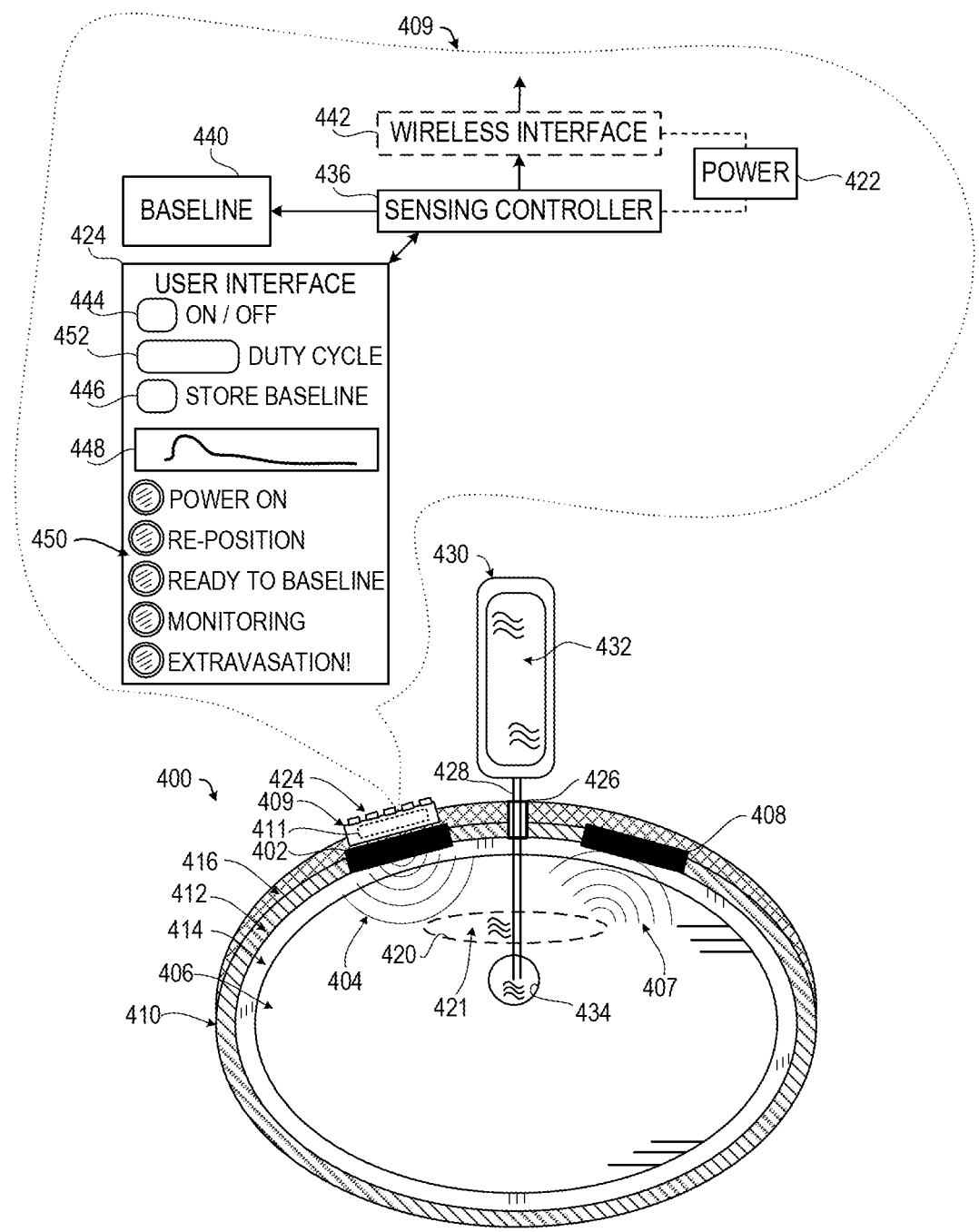
FIG. 4 is a schematic block diagram of an integrated wound and sensor assembly for detecting a change in a fluid level in tissue, according to one aspect.

In FIG. 4, an exemplary aspect is depicted for an integrated device 400 for implementing aspects described above for the integrated device 100 (FIGS. 1-3). The integrated device 400 has a transmitter 402 for directing transmitted power 404 into tissue of a body portion 406 for being received as received power 407 by a sensor or receiver 408. Integrated sensor circuitry 409 within a housing 411 is attached to a substrate 410. The substrate 410 may comprise a structural layer 412, an underlying dressing layer 414, and an overlying isolation layer 416.

At a baseline time, the transmitted power 404 encounters a baseline condition of fluid level. At a subsequent current time, when fluid is being provided into a vascular structure 434, the transmitted power 404 may encounter a change, depicted at 420 as an increase (extravasation, infiltration, etc.) in fluid 421. A power supply 422, such as a rechargeable battery, is provided as part of the integrated sensor circuitry 409. An indicator 424, depicted as a user interface, is responsive to a sensing controller 436 to indicate a detected change in a fluid level in the body portion 406 from extravasation or infiltration. The sensing controller 436 may define a signal processor.

A fluid guiding component 426, such as a piece of tape or a Tagaderm (an adhesive device to hold and protect a catheter entrance hole in skin) receives a conduit 428 (e.g., needle, catheter, etc.) of a fluid injector, infuser, or IV supply 430 for transferring fluid 432 to the vascular structure 434 of the body portion 406.

A nurse or technician may adjust, such as via a duty cycle control 452 on the user interface 424, a rate of activation of the transmitter 402 in relation to a rate of fluid 432 being transferred through the conduit 428 so as to minimize power consumption. For example, presuming X volume of accidentally injected fluid within a patient is considered unacceptable, e.g., 2 ml, and fluid is being or about to be injected into the patient at a desired rate of Y volume/time, e.g., 1 ml/hour, then a nurse or technician may use the following formula to define a time period between activation events of the transmitter 402:

Time period between activation events of transmitter 402=[X volume of unacceptable injected fluid]/[injection rate of Y volume/time]÷2(Safety factor).

The rate of activation of the transmitter 402(number of activations per unit time)=1/time period between activation events of the transmitter.

It is also contemplated that the sensing controller 436 may be used to determine the rate of activation of the transmitter 402 using the above formulas after a nurse or technician has input, via the user interface 424, an unacceptable injected volume (X volume) and the current fluid injection rate (Y volume/time).

In another exemplary aspect, the user interface 424 includes an activation control 444, a store baseline control 446, a depiction 448 for the received power 407, and status indicators 450. For example, the status indicators 450 can indicate an activated or deactivated state, a malfunctioning state (e.g., "reposition needed"), a ready to baseline state, a monitoring state, and a fluid detected state (e.g., "extravasation alert").

In an additional exemplary aspect, the depiction 448 for the received power 407 indicates a change in received power from a baseline power.

Figure 5:
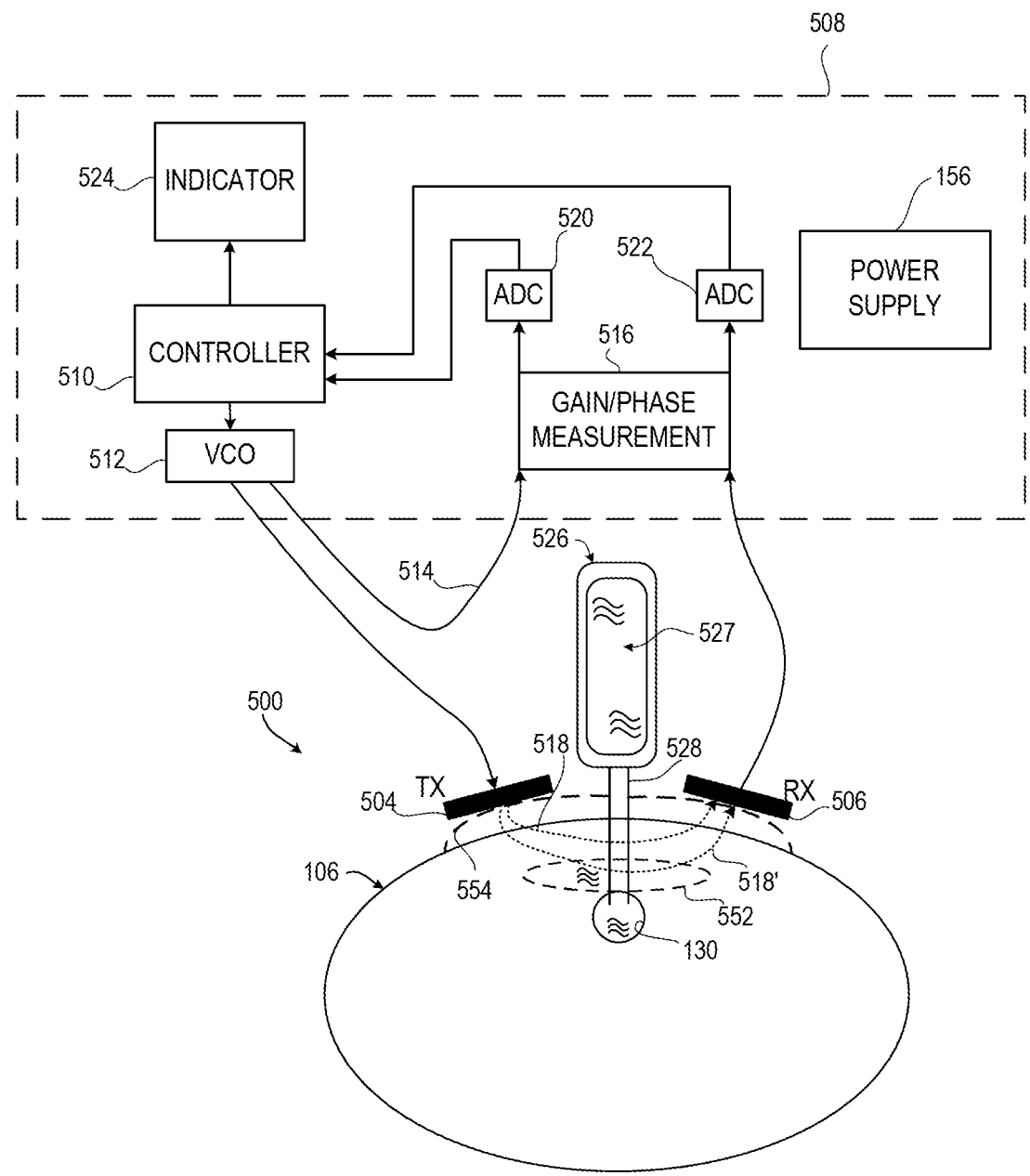
FIG. 5 is a schematic block diagram of a Radio Frequency (RF) integrated device, according to one aspect.

In FIG. 5, in a yet another exemplary aspect, the transmitter comprises a Radio Frequency (RF) transmitter and the sensor comprises an RF sensor.

In FIG. 5, in an exemplary embodiment of the integrated device 100 (FIG. 1), an RF integrated device 500 has RF transmit (TX) antenna(s) 504 that are driven and RF receive (RX) antenna(s) 506 that are read by an Application Specific Integrated Circuit (ASIC) or miniaturized, low-power circuitry 508 including a controller 510, such as a low-power microprocessor, Digital Signal Processor (DSP), or Field Programmable Gate Array (FPGA). The controller 510 drives an RF Voltage Controlled Oscillator (VCO) 512 or digital frequency synthesis circuit so as to sweep across the RF frequency range of interest, such as 300 MHz to approximately 30 GHz, and more particularly up to 10 GHz. The transmit antenna(s) 504 of the RF device 500 are then driven by the VCO 512 and the same signal is split as a reference signal 514 to a gain/phase measurement circuit/IC 516 (e.g., "AD8302," commercially available from Analog Devices). The RX antenna(s) 506 return a signal corresponding to the power 518, 518' (power 518' passes through fluid 552) propagated through the tissue to the gain/phase measurement circuit/IC 516, which then sends voltages (representing gain/loss and phase information for the TX and RX signals) to two Analog-to-Digital Converters (ADC) 520, 522, which then digitize the corresponding voltage information to the controller 510. The controller 510 can perform digital signal processing and direct an indicator 524.

A reference signal 514 may be generated because the VCO 512 outputs a signal that may vary over time.

In order to sense an extravasation or infiltration, the controller 510 compares a first ratio of the returned signal from the RX antenna(s) 506 to the reference signal 514 (during fluid injection) with a second ratio of the returned signal from the RX antenna(s) 506 to the reference signal 514 (taken during a baseline detection operation, e.g., just before fluid is injected into the body portion). When the first ratio is a predefined percentage, e.g., 90% or less, of the second ratio, then the controller 510 determines that an unacceptable extravasation/infiltration has occurred.

In use, a fluid supply 526 (e.g., infuser supply, contrast agent injector, IV drip, etc.) provides fluid 527 via a conduit 528 (e.g., catheter, needle, etc.) to a vascular body 130 of the body portion 102. As depicted at 552, extravasation or infiltration can cause an increase in a level of fluid that directly affects a signal 518' propagating through the tissue, which typically results in a reduction in the amount of power received by the RX antenna(s) 506. Alternatively, a resulting change in dimensions of the body portion 106, as depicted at 534, can cause a change in the signal 518'.

The rate at which the RF device 500 is active (e.g., rate of RF sweeps, etc.) can be optimized between power consumption and a prudent rate of monitoring in order to extend the service life of the power supply.

Figure 6:
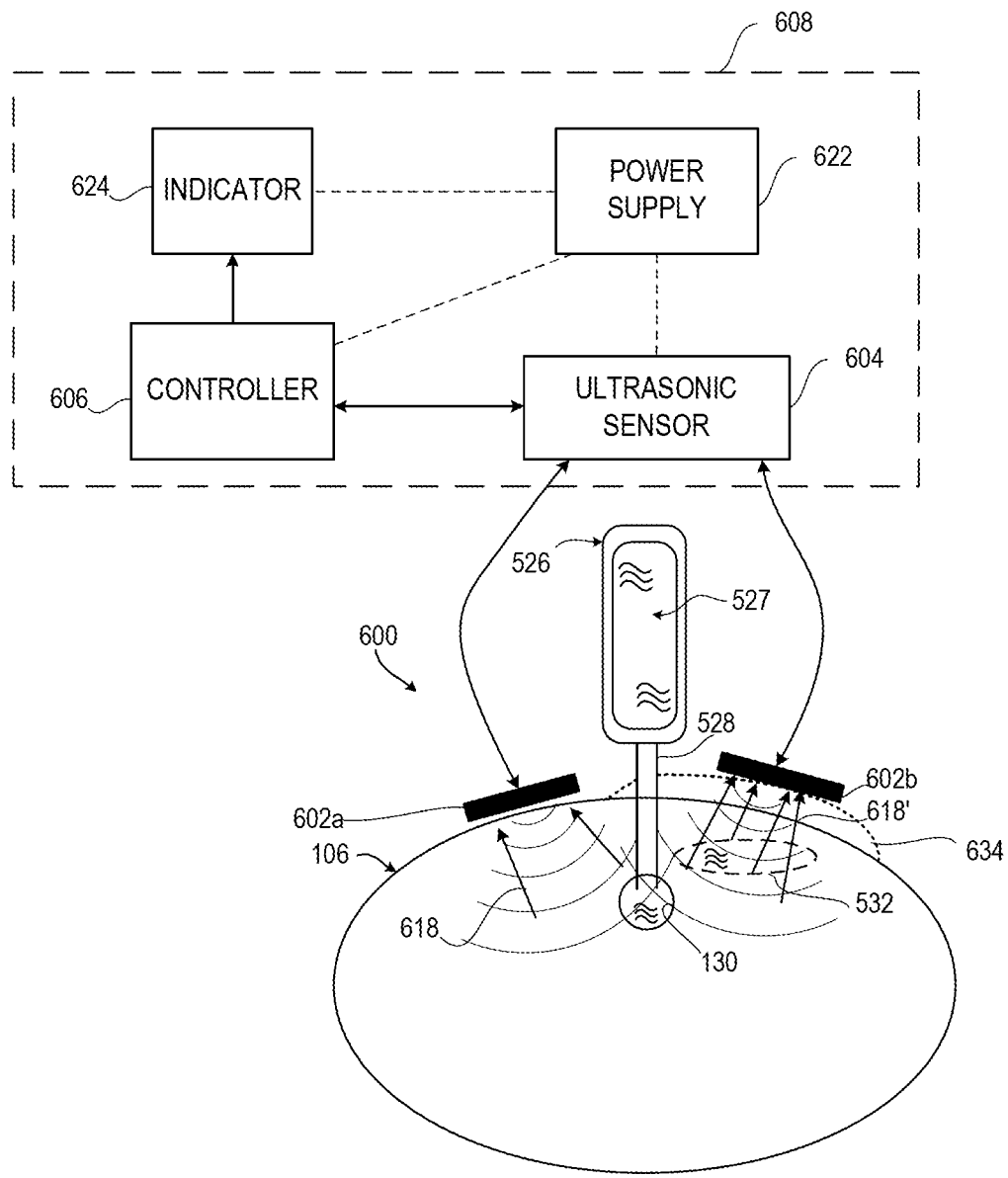
FIG. 6 is a schematic block diagram of an alternative ultrasonic integrated device, according to one aspect.

In FIG. 6, in yet a further exemplary aspect, the integrated device 100 (FIG. 1) can comprise an ultrasonic integrated device 600. In a particular aspect, the ultrasonic integrated device 600 is further for detecting the change in the fluid level in the body portion from extravasation or infiltration based upon changes in amplitude and phase for propagation of the directed acoustic power. The ultrasonic integrated device 600 has ultrasonic transceiving antenna(s) 602a, 602b that are driven and are read by an ultrasonic sensor 604 under the control of a controller 606 that reports via an indicator 624.

In use, the fluid supply 526 (e.g., infuser supply, contrast agent injector, IV drip, etc.) provides fluid 527 via the conduit 528 (e.g., catheter, needle, etc.) to a vascular body 530 of the body portion 106. In a baseline state, the ultrasonic transceiving antenna(s) 602a transmits and receives an ultrasonic signal 618. Extravasation or infiltration can cause an increase in a level of fluid, as depicted at 532, that directly affects an ultrasonic signal 618' sensed by the ultrasonic transceiving antenna(s) 602b due to a resulting change in dimensions of the body portion 102, as depicted at 634, or due to acoustic properties of the fluid relative to surrounding tissue. Time domain (pulse) mode of operation with an ultrasonic transceiver will lend itself to this method. Also, by using a separate ultrasonic transducer for transmission and a separate transducer for reception, one can use continuous wave (CW), as known to those skilled in the art, to collect frequency domain data. This frequency domain data can then be transformed into the time domain for gating (to remove unwanted reflections at the skin boundary or further structures outside of the region of interest for example) and then analysis of the signal of interest (reflections within the tissue). If the timing or amplitude of the reflections within the tissue change as compared to a baseline, then this is indicative of fluid being introduced which is directly, or indirectly, affecting the signals returning from within the tissue.

Figure 7:
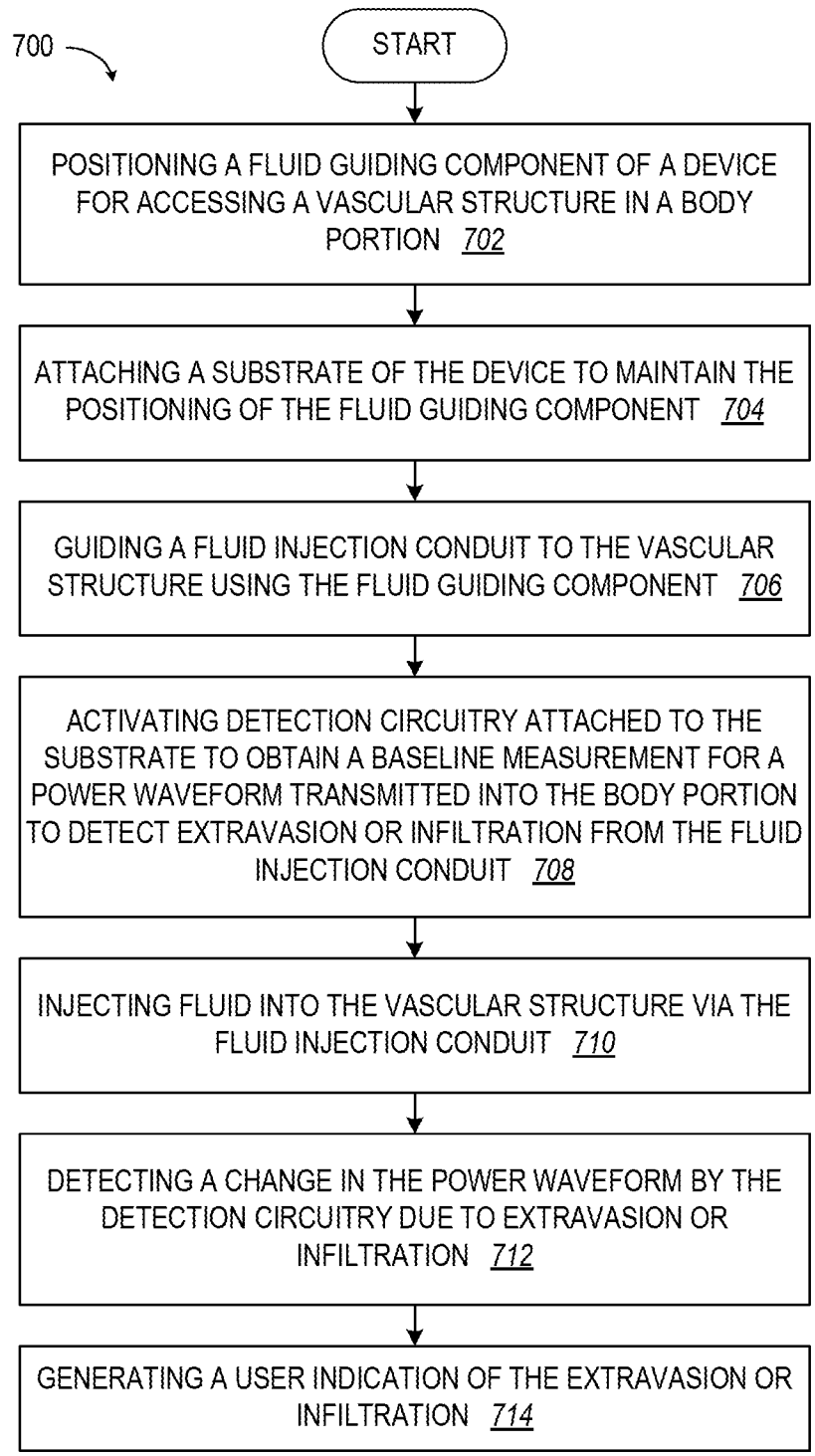
FIG. 7 is a flow diagram of a methodology for detecting a change in the fluid level of tissue, according to one aspect.

In FIG. 7, a method for detecting extravasation or infiltration is depicted. A fluid guiding component of a device is positioned for accessing a vascular structure in a body portion (block 702). A substrate of the device is attached to maintain the positioning of the fluid guiding component (block 704). A fluid injection conduit is guided to the vascular structure using the fluid guiding component (block 706). Detection circuitry attached to the substrate is activated to obtain a baseline measurement for an power waveform transmitted into the body portion to detect extravasation or infiltration from the fluid injection conduit (block 708). Fluid is injected into the vascular structure via the fluid injection conduit (block 710). A change in a current power waveform from the baseline waveform is detected by the detection circuitry due to extravasation or infiltration (block 712). A user indication of the extravasation or infiltration is generated (block 714).

In an exemplary aspect, generating the user indication is by activating a user interface attached to the substrate. In a particular aspect, a current measurement for indicating on the user interface is generated.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

What is claimed is:

1. An integrated device configured to detect extravasation, the integrated device comprising:
    a flexible substrate comprising (i) a first layer configured to contact an outer surface of a body portion, and (ii) a second layer coupled to the first layer and configured to releasably mount, at a first side and via an adhesive border, the flexible substrate to the outer surface of the body portion, wherein the flexible substrate is configured to support:
        a transmitter configured to direct power into the body portion;
        a sensor configured to receive the power transmitted through the body portion;
        a signal processor and a power supply coupled to the transmitter and the sensor; and
        an indicator responsive to the signal processor; and
    a fluid guiding component positioned on the flexible substrate,
    wherein the signal processor is configured to:
        define, prior to insertion of fluid into a vascular structure of the body portion, a first signal indicating a baseline condition of a fluid level in the body portion, the first signal defining an extravasation or infiltration threshold;
        define, at a subsequent time during insertion of the fluid into the vascular structure, a second signal;
        compare the second signal to the first signal by:
            generating a first ratio of the first signal to a reference signal;
            generating a second ratio of the second signal to the reference signal; and
            comparing the first and second ratios; and
        when the second signal is less than or equal to the first signal and the second ratio is a predefined percentage of the first ratio, reduce an amount of the fluid being inserted into the vascular structure, and wherein the indicator is configured to indicate the change in the baseline condition of the fluid level in the body portion from extravasation or infiltration.

2. A method for detecting extravasation or infiltration, comprising:
   mounting an integrated device to an outer surface of a body portion, the integrated device configured to detect extravasation or infiltration, the integrated device comprising:
      a flexible substrate comprising (i) a first layer configured to contact an outer surface of the body portion, and (ii) a second layer coupled to the first layer and configured to releasably mount, at a first side and via an adhesive border, the flexible substrate to the outer surface of the body portion,
      wherein the flexible substrate is configured to support integrated circuitry comprising a transmitter, a sensor, a signal processor, a power supply, and an indicator;
   inserting a fluid injection conduit into a vascular structure in the body portion;
   activating the integrated circuitry to obtain a baseline measurement for a power waveform transmitted into the body portion, the baseline measurement defining a first signal indicating a baseline condition of a fluid level in the body portion;
   injecting fluid into the vascular structure via the fluid injection conduit at a fluid injection rate;
   activating the integrated circuitry to obtain a subsequent measurement for the power waveform transmitted into the body portion, the subsequent measurement defining a second signal;
   detecting, by the integrated circuitry, a change in the baseline condition based on a comparison of the second signal to the first signal, wherein the comparison comprises:
      generating a first ratio of the first signal to a reference signal;
      generating a second ratio of the second signal to the reference signal; and
      comparing the first and second ratios; and
   when the second signal is less than or equal to the first signal and the second ratio is a predefined percentage of the first ratio, reducing the fluid injection rate; and
   indicating, by the indicator, the change in the baseline condition of the fluid level in the body portion from extravasation or infiltration.

3. An integrated device configured to detect extravasation or infiltration, the integrated device comprising:
   a flexible substrate comprising (i) a first layer configured to contact an outer surface of a body portion, and (ii) a second layer coupled to the first layer and configured to releasably mount, at a first side and via an adhesive border, the flexible substrate to the outer surface of the body portion, wherein the flexible substrate is configured to support:
      a transmitter configured to direct power into the body portion;
      a sensor configured to receive the power transmitted through the body portion;
      at least one of a signal processor or a power supply coupled to the transmitter and the sensor; and
      an indicator responsive to the signal processor, and
   a fluid guiding component positioned on the flexible substrate;
   wherein the signal processor is configured to:
      define, prior to insertion of fluid into the body portion, a first signal indicating a baseline condition of a fluid level in the body portion, the first signal defining an extravasation or infiltration threshold;
      define, at a subsequent time during insertion of the fluid into the body portion, a second signal;
      compare the second signal to the first signal; and
      when the second signal is less than or equal to the first signal, reduce an amount of the fluid being inserted into the body portion, and
   wherein the indicator comprises a user interface configured to provide a notification that the second signal is less than or equal to the first signal, and
   wherein the signal processor is further configured to determine a duty cycle for the integrated circuitry required to effectively monitor the fluid being injected into the body portion at the fluid injection rate and to minimize power consumption.

4. The integrated device of claim 3, further comprising a marked transparent substrate for exposing a vascular structure of the body portion.

5. The integrated device of claim 3, wherein the transmitter comprises a Radio Frequency (RF) transmitter and the sensor comprises an RF sensor.

6. The integrated device of claim 5, further comprising an RF absorbing layer externally disposed over at least a portion of the transmitter, sensor and substrate.

7. The integrated device of claim 3, wherein the transmitter comprises an ultrasonic transmitter and the sensor comprises an ultrasonic sensor.

8. The integrated device of claim 7, wherein the signal processor is further configured to detect changes in amplitude and phase for propagation of the power directed into the body portion.

9. The integrated device of claim 3, wherein the indicator is further configured to indicate a selected one of a deactivated state, a baseline state, and a fluid detected state.

10. The integrated device of claim 3, wherein the indicator is further configured to indicate a range of sensed values of the power sensed at the sensor.

11. The integrated device of claim 3, wherein the substrate comprises wound dressing material.

12. The integrated device of claim 3, wherein the substrate is configured to support the signal processor and the power supply.

13. The integrated device of claim 3, wherein determining the duty cycle comprises determining a rate of activation of the integration circuitry based on the fluid injection rate and an unacceptable volume of accidentally injected fluid.

14. The integrated device of claim 5, wherein the substrate comprises an isolating layer containing an iron filler to reduce stray RF power.

15. The integrated device of claim 1, wherein the predefined percentage is 90% or less.

16. A method for detecting extravasation or infiltration, comprising:
   mounting an integrated device to an outer surface of a body portion, the integrated device configured to detect extravasation or infiltration, the integrated device comprising:
      a flexible substrate comprising (i) a first layer configured to contact an outer surface of the body portion, and (ii) a second layer coupled to the first layer and configured to releasably mount, at a first side and via an adhesive border, the flexible substrate to the outer surface of the body portion, wherein the flexible substrate is configured to support integrated circuitry comprising a transmitter, a sensor, a signal processor, a power supply, and an indicator;

inserting a fluid injection conduit into a vascular structure in the body portion;

activating the integrated circuitry to obtain a baseline measurement for a power waveform transmitted into the body portion, the baseline measurement defining a first signal indicating a baseline condition of a fluid level in the body portion;

injecting fluid into the vascular structure via the fluid injection conduit at a fluid injection rate;

activating the integrated circuitry to obtain a subsequent measurement for the power waveform transmitted into the body portion, the subsequent measurement defining a second signal;

detecting, by the integrated circuitry, a change in the baseline condition by comparing the second signal to the first signal; and when the second signal is less than or equal to the first signal, reducing the fluid injection rate;

indicating, by the indicator, the change in the baseline condition of the fluid level in the body portion from extravasation or infiltration; and determining a duty cycle for the integrated circuitry required to effectively monitor the fluid being injected into the body portion at the fluid injection rate and to minimize power consumption.

17. The method of claim 16, wherein determining the duty cycle comprises determining a rate of activation of the integration circuitry based on the fluid injection rate and an unacceptable volume of accidentally injected fluid.

* * * * *